United States Patent [19]

Kitahara et al.

[11] Patent Number: Plant 7,192

[45] Date of Patent: Mar. 13, 1990

[54] PLUM TREE, "ROYAL STAR"

[76] Inventors: Lawrence K. Kitahara, 2455 Bliss Ave., Clovis, Calif., 93612; Kei Kitahara, 242 W. Palm Ave., Reedley, Calif. 93654

[21] Appl. No.: 318,054

[22] Filed: Feb. 17, 1989

[51] Int. Cl.[4] ..... A01H 5/00

[52] U.S. Cl. ..... Plt./38

[58] Field of Search ..... Plt./38

[56] References Cited

U.S. PATENT DOCUMENTS

Plt. 2,415 6/1964 Anderson ..... Plt. 38

Plt. 2,747 6/1967 Garabedian ..... Plt. 38

Plt. 5,912 3/1987 Garabedian ..... Plt. 38

*Primary Examiner*—Howard J. Locker

*Attorney, Agent, or Firm*—Worrel & Worrel

[57] ABSTRACT

A new and distinct variety of plum tree denominated varietally as "Royal Star" and which is characterized as to novelty by its large ovate shape with a blue color, a pink to red flesh color, a tight cling type stone and above average fruit quality ripening in the last week of August to the first week of September under the ecological conditions prevailing in Kingsburg in the San Joaquin Valley of California.

1 Drawing Sheet

BACKGROUND OF THE NEW VARIETY

The present invention relates to a new and distinct variety of plum tree, hereinafter denominated varietally as "Royal Star", and more particularly to a plum tree which is somewhat broadly similar to the commercial plum variety "Angeleno" (U.S. Plant Pat. No. 2,747) in its exterior blue color and similar late date of maturity ripening in the last week of August to the first week of September, but from which it is distinguished in its ovate fruit shape, pink to red flesh color, tight cling type stone and above average fruit quality.

The development of commercially successful varieties of fruit bearing trees entails rigorous and extensive test procedures, careful nurturing and meticulous observation over many years. Frequently many hundreds or thousands of seedlings must be observed and the observations recorded over lengthy periods of time before even one new variety can be developed which is worthy of reproduction on a commercial scale. In other instances, the keen powers of observation of a skilled plant breeder will locate, for example, a chance seedling which possesses those attributes warranting development. Such serendipitous discoveries are rare and yet have played a significant role in the development of present commercial varieties.

The plum tree of the present invention is an open-pollinated chance seedling of unknown parentage which was discovered within a cultivated area of the applicant's property at 12199 South Zediker Avenue in Kingsburg, Calif.

ORIGIN AND ASEXUAL REPRODUCTION OF THE NEW VARIETY

The "Royal Star" plum tree was discovered by the inventors as an open-pollinated seedling of unknown parentage growing within the cultivated area of the property of Kei Kitahara at 12199 South Zediker Avenue in Kingsburg, Fresno County, Calif. The inventors noticed the desirable characteristics of the subject variety and in 1983 asexually reproducted the new variety by grafting bud wood from the chance seedling onto mature test trees located at the same site in Kingsburg, Calif. The first asexual reproduction resulted in progeny which produced their first fruit in 1985 and were observed to possess the same distinctive charcteristics as the original chance seedling of the subject variety.

SUMMARY OF THE NEW VARIETY

The "Royal Star" plum tree is characterized by bearing fruit of a large ovate shape with blue color, a pink to red flesh color, a tight cling type stone and above average fruit quality maturing extra late in the growing season, being somewhat similar to the Angeleno Plum Tree U.S. Plant Pat. No. 2,747) in the external color of the fruit and late date of maturity, but distinguished therefrom in that the "Angeleno" plum tree fruit is roundish-oblate with yellow-amber flesh color and is a semi-free stone having a very dry, bland flavor.

BRIEF DESCRIPTION OF THE DRAWING

The accompanying drawing is a color photograph of a characteristic twig bearing leaves typical of the new variety, several mature fruit showing their external coloration sufficiently matured for harvesting and shipment, one fruit of the subject variety dissected in the suture plane and parted to display on one half the stone in the stone cavity and the stone cavity on the other half.

DETAILED DESCRIPTION

Referring more specifically to the pomological details of this new and distinct variety of plum tree, the following has been observed under the ecological conditions prevailing in the orchard of the inventor located in Kingsburg, Calif. All major color code designations are by reference to the Dictionary of Color by Maerz and Paul, Second Edition, published in 1950. Common color designations are also employed in some instances.

TREE

Generally:

*Size.*—Average.

*Vigor.*—Vigorous.

*Form.*—Upright and spreading with eventual form and density determined by pruning.

*Productivity.*—Productive.

*Regularity of bearing.*—Regular.

*General health.*—Hardy under normal climatic conditions existing in the San Joaquin Valley of California.

Trunk:

*Size.*—Medium.

*Surface texture.*—Moderately rough with considerable scarfskin present.

*Color.*—Brown-grey (8-C-8).

*Lenticels.*—Numerous and medium sized.

Branches:

*Thickness.*—Average.

*Surface texture.*—Average.

*Color.*—Mature branches are grey-brown (8-C-9). Immature branches are green (21-K-6) to light brown (15-J-10).

LEAVES

Size: Medium. Leaf dimension measurements taken from leaves growing at midpoint of actively growing current season's shoots.

*Average length.*—Approximately 10.7 cm.

*Average width.*—Approximately 4.3 cm.

Thickness: Above average for species.

Form: Broadly lanceolate and often slightly asymmetrical. Leaves slightly folded inwardly from midrib. Leaf apex is acute and most often twisted.

Color: Upper leaf surface is deep green (23-L-6). Lower leaf surface is grey-green (21-E-2).

Margins: Coarsely crenate, often doubly and occasionally triply crenate from mid-margin to apex. More finely crenate from mid-margin to base.

Petiole: Medium size, 9 to 11 mm in length. Average thickness 2 mm. Petiole color a light grey-green (17-E-3) strongly tinged a fawn color (14-A-7).

Glands: Very small in size. Two to four glands most often present, alternate in position on base of leaf margin and most often globose in form.

Gland color: Light green (18-H-4), darkening and deteriorating with age.

Stipules: Medium to small in size averaging 5 to 6 mm in length. Narrow lanceolate in form. Many stipules are persistent.

Stipule color: Light green (10-J-7) often tinged red and darkening with age.

FLOWERS

This description has been developed from notes taken on Feb. 18, 1986 in orchard in Kingsburg, Calif.

Flower buds: Conic in form and of average size for species. Usually a minimum of two flower buds present per node.

Date of full bloom: Feb. 15, 1986.

Date of bloom generally: Full bloom late for species and late in relation to other commercial Japanese plum varieties growing in the San Joaquin Valley of California.

Flower size: Medium. Average flower diameter 16 to 18 mm when fully open.

Bloom quantity: Abundant and uniform in opening.

Flower petals: Medium in size, 7 to 8 mm in length, 6 to 7.5 mm in width. Globose occasionally to slightly obovate in form with a short claw. Petal margins undulate and entire petal cupped inward, even at full maturity.

Flower petal color: White (1-A-1).

Pedicel: Short, average length 4 to 5 mm. Average thickness 0.5 mm. Glabrous.

Pedicel color: Bright green (18-I-5).

Nectaries color: Gold-brown (14-F-12) in young flowers. Brown (15-H-9) with a slight greenish caste in mature flowers.

Anthers: Medium size. Pollen abundant.

Anther color: Light orange to salmon (12-C-10) dorsally. Straw colored (11-G-4) ventrally. Pollen yellow (17-J-1) in color.

Stamens: Average in length.

Stamen color: White (1-A-1).

Pistil: Medium length, 6 to 7 mm including ovary.

Pistil color: Light yellow-green (17-G-2).

FRUIT

Maturity: Described on Aug. 30, 1985 from fully mature fruit harvested in a firm ripe condition at the orchard in Kingsburg, Calif. The subject tree was fully cropped. Date of first pick was Aug. 30, 1985. Fruit hangs well on tree with date of last pick approximately ten days later on Sept. 8, 1985.

Size: Large and uniform. Average cheek diameter 56.8 mm. Average suture diameter 54.2 mm. Average axial diameter 53.5 mm.

Form: Slightly variable but most frequently broadly ovate in lateral aspect. Nearly globose in apical aspect. Asymmetrical with one half of fruit often larger than the other.

Suture: A very thin line extending from base to apex at times blending well with surrounding skin coloration. At other times suture darkens to a distinct blue-black (48-H-9) line about 1.0 to 1.5 mm in thickness. Suture narrows and deepens over basal shoulder.

Ventral surface: Variable. At times smoothly rounded. At other times slightly lipped with one side larger.

Stem cavity: Small narrow oval, relatively deep at 9 to 10 mm. Average width 10 to 14 mm. Average length 14 to 15 mm. Some folding of the suture on ventral side within the cavity.

Base: Slightly truncate. Base oblique to fruit axis. Shorter on dorsal suture side.

Fruit apex: Variable. Some fruit rounded while others slightly prolonged and raised. Pistil point slightly oblique. Distinct depression beyond the pistil point opposite ventral suture side.

Stem: Short to medium in length, average 10 to 12 mm. Stem thickness average 1.5 to 2.0 mm.

Stem color: Variable from green (17-H-4) to brown (7-E-10).

Skin:

*Thickness.*—Medium (average).

*Texture.*—Medium (average).

*Acidity.*—Low.

*Tenacious to flesh.*—Yes.

*Tendency to crack.*—None observed.

*Color.*—A uniform overall dark blue-black (48-H-9) lightening in some fruit to a garnet red (8-J-5), especially over basal shoulders. Usually no base or ground color visible.

*Surface character.*—Fruit surface uniformly covered with a heavy grey-blue bloom. Surface very smooth and almost devoid of any prominent flecking or dots. Skin lenticels present, but very small and obscure.

Flesh:

*Color.*—Basic flesh color is pink (3-G-9) with numerous prominent red fibers (3-J-10) extending through the flesh from pit cavity outward to skin. Flesh color slightly darker pink-orange (3-E-10) in some areas just under the skin surface and within the pit cavity. Flesh color is slightly lighter pink (2-B-9) in area extending 5 to 6 mm outward from pit cavity. All areas of flesh darken and become more pink to red with advancing maturity.

*Texture.*—Firm, medium to slightly coarse. Moderately juicy especially with full maturity.

*Fibers.*—Numerous moderately long red (3-J-10) fibers very prominent in flesh. Fine textured.

*Ripening.*—Ripens evenly.

*Flavor.*—Mild and pleasant.

*Aroma.*—Slight.

*Eating quality.—Good, above average.*

STONE

Attachment: Clingstone. Held tightly in pit cavity.

Size: Medium. Average length 25 to 26 mm. Average width 17 to 19 mm. Average thickness 9 to 11 mm.

Fibers: Numerous short fibers firmly attached to stone both laterally and along both sutures.

Form: Irregular but most closely approximating an oval.

Base: Rounded over ventral suture side. More truncate along dorsal suture side. Base angle variable from right angle to stone axis to very slightly oblique to stone axis.

Hilum: Very small, oval and only slightly eroded.

Apex: Acute with short sharp tip.

Stone sides: Variable from equal to slightly unequal.

Stone surface: Moderately rough with a few low ridges over stone sides. Low ridges present laterally over basal shoulders converging basally.

Ventral edge: A low wing present extending from apex to base somewhat more protruding over basal shoulder. Two narrow but distinct grooves present, one on each side of wing more or less parallel to ventral edge but converging apically and basally, Upper (apical) 8 mm of suture is nearly concave.

Dorsal edge: Small narrow groove from base to apex narrowing substantially over apical shoulder. Apical shoulder also substantially more jagged than basal shoulder of dorsal edge.

Stone color: Dry color tan (11-D-5) with light tinting of red stain.

Tendency to split: No tendency to split observed.

Fruit use:

A fresh market plum for local use and for long distance shipping.

Keeping quality: Good.

Although the new variety of plum possesses the described charcteristics when grown under the ecological conditions prevailing in Kingsburg, Calif., in the central part of the San Joaquin Valley, it is to be understood that variations of the usual magnitude and characteristics incident to changes in growing conditions, fertilization, pruning and pest control are to be expected.

Having thus described and illustrated our new variety of plum tree, what is claimed as new and desired to be secured by Letters Patent is:

1. A new and distinct variety of Plum Tree substantially as illustrated and described and which bears fruit somewhat similar to that of the Angeleno Plum Tree (U.S. Plant Pat. No. 2747) in the external color of the fruit and the late date of maturity, but which is distinguished therefrom and characterized principally as to novelty in that the fruit is of a large ovate shape with a blue color, a pink to red flesh color, a tight cling type stone and above average fruit quality, the fruit ripening in the last week of August to the first week of September under the ecological conditions prevailing in Kingsburg, Calif.

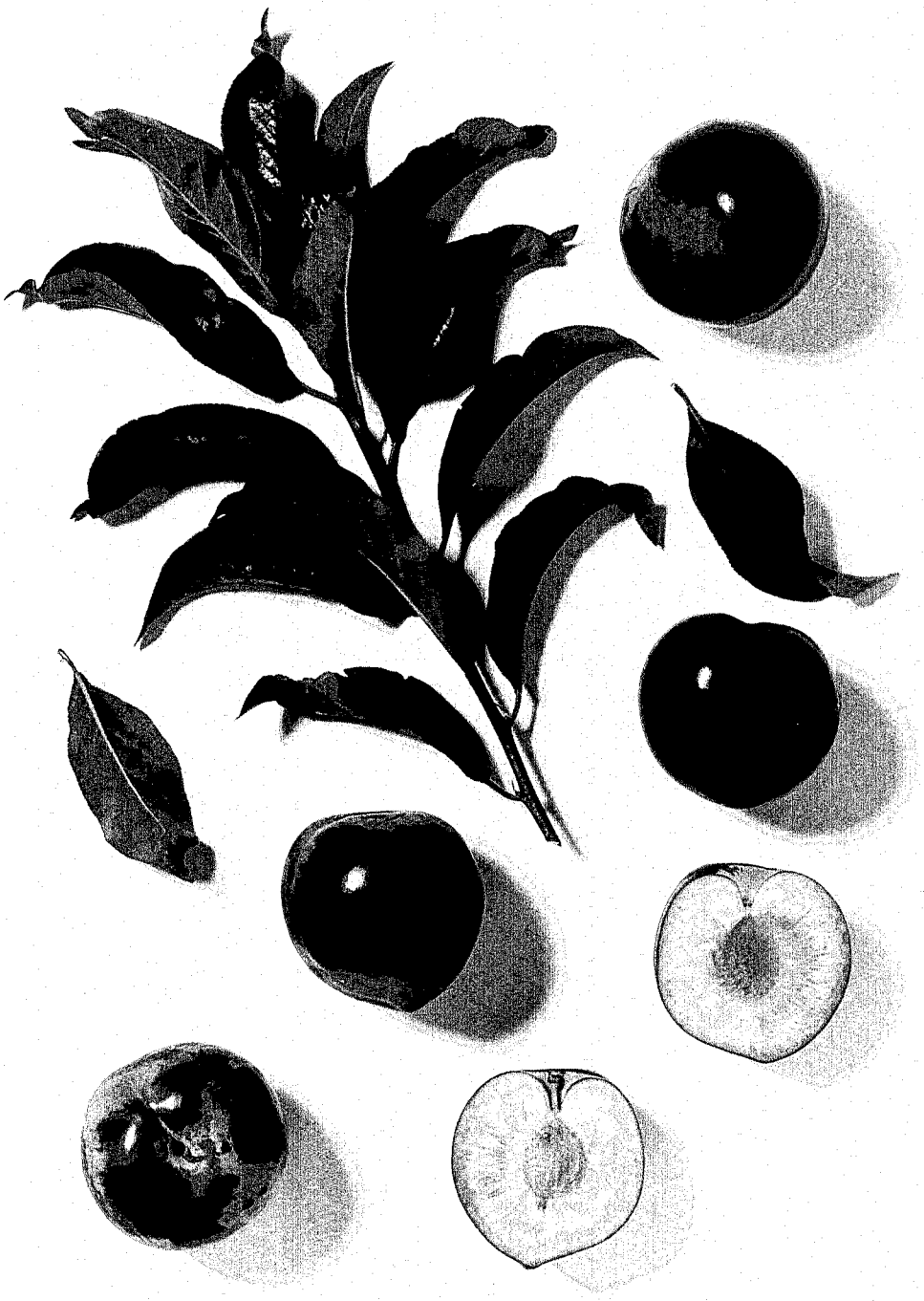

* * * * *